United States Patent [19]

Gula et al.

[11] 3,995,628
[45] Dec. 7, 1976

[54] CATHETER INSERTION DEVICE

[75] Inventors: John A. Gula, Dallas; Thomas C. Thompson, Richardson; John Ellis Kling; John L. Center, both of Dallas, all of Tex.; Bert S. Bodnar, Park Ridge, Ill.

[73] Assignee: Travenol Laboratories, Inc., Dallas, Tex.

[22] Filed: Apr. 25, 1975

[21] Appl. No.: 571,496

[52] U.S. Cl. .......................................... 128/214.4
[51] Int. Cl.[2] ........................................ F24C 15/10
[58] Field of Search ............ 128/214.4; 132/89, 91

[56] References Cited

UNITED STATES PATENTS

| | | | |
|---|---|---|---|
| 2,711,734 | 6/1955 | Moe | 128/276 |
| 3,561,445 | 2/1971 | Katerndahl | 128/214.4 |
| 3,730,835 | 5/1973 | Leeper et al. | 128/349 R |
| 3,804,102 | 4/1974 | Bennington | 132/92 A |
| 3,827,434 | 8/1974 | Thompson et al. | 128/214.4 |
| 3,861,396 | 1/1975 | Vaillancourt | 128/349 R |
| 3,901,251 | 8/1975 | Johnston | 132/91 |
| 3,908,677 | 9/1975 | Beach | 132/91 |

Primary Examiner—G.E. McNeill
Attorney, Agent, or Firm—Richards, Harris and Medlock

[57] ABSTRACT

A catheter insertion device utilizing a catheter wound inside a two-piece generally cylindrical dispenser and extending outwardly into a slotted needle secured to an outlet from the dispenser; a stiffener comprising a closely-wound wire helix which surrounds a central straight wire is positioned inside the catheter; the dispenser is composed of two relatively rotatable parts, one a relatively flat base having a slot communicating with the slotted needle, the other a receptacle having an inwardly-facing wall which engages the catheter; the receptacle is releasably and rotatably held to the base by a central spindle extending upwardly from the base member through a hole in the top of the receptacle; a flexible feed guide extends from the base adjacent the dispenser outlet and guides the catheter toward the outlet; the guide is engageable with a stop to positively prevent further rotation of the receptacle at a predetermined point when the proximal end of the catheter nears the outlet; the dispenser spindle is split into yieldable fingers at its outer end and provided with a circumferential detent which engages the receptacle; a cooperating release button positioned atop the spindle may be pressed to urge the fingers of the spindle together and assist in releasing the receptacle from the spindle detent after insertion.

20 Claims, 16 Drawing Figures

CATHETER INSERTION DEVICE

This invention relates to a device for the insertion of a catheter into the vascular system of a patient, and more particularly to such devices of the type which employ a needle secured to a dispenser having a rotatable catheter receptacle to forward the catheter through the needle.

Although dispensing devices employing a rotating receptacle action similar to that disclosed in this application have been known in the prior art (e.g., U.S. Pat. Nos. 2,685,097 and 3,561,445), no device known to applicants has achieved the superior results flowing from the novel combination disclosed herein.

The advantages of the device disclosed herein are most marked with regard to applications in which relatively long catheters are required. An example of such a situation is the introduction of a catheter to forward the distal end thereof to the central veins of the chest, through an entry made in the peripheral vessels, such as those in the arm. Such an application may require as much as a twenty-four inch catheter length. The utilization of the device disclosed herein represents a significant stride forward in the emplacing of such catheters. The device may also be used with medium length and long catheters smaller than 24 inches, particularly those over about eight inches.

The device disclosed herein is particularly advantageous in connection with the incorporation of catheters formed from silicone elastomer tubing, although the invention is not limited to the use of such tubing. The desirable properties of silicone elastomer tubing for use in catheters for intravenous infusion of fluids or other medical applications have been known for over twenty-five years. The materials from which tubing of this type are fabricated, for example, a silicone elastomer marketed under the trademark "SILASTIC", are marked by a high degree of body compatibility compared to other materials from which catheters have been and are formed, such as polyethylene, "Teflon", and vinyl. The silicone elastomers are relatively inert to organic tissues and fluids, non-clotting as to the blood and are highly flexible so as to reduce the trauma involved in their insertion and maintenance in the body. It is possible to maintain a silicone elastomer catheter implanted in the body for a longer period of time than with other types of tubing. The necessity for frequent removal and reintroduction of catheters is a marked disadvantage in almost any medical application.

One particular difficulty experienced in the past with respect to inserting and forwarding relatively long silicone elastomer catheters has been the difficulty in providing sufficient stiffness and control over the catheter during forwarding while avoiding the dangers of piercing the catheter or causing undue trauma to the patient's system. The device disclosed herein incorporates a stiffening mechanism and a feed guide which cooperate with the catheter and the dispensing apparatus to give good control over forwarding of the silicone elastomer catheter while minimizing the dangers of piercing and trauma. It is particularly advantageous in exceptionally long catheter applications, since the stiffener and controlled dispensing apparatus cooperate to effectively forward the catheter, even in instances where the path for the catheter provides resistance. The forwarding action of the dispenser appears to cause the stiffener to slide out through the distal end of the silicone elastomer catheter and guide the catheter forward. The stiffener may be withdrawn smoothly after insertion because of the cooperation between the helical stiffener employed and the silicone elastomer catheter.

One danger which is present in some needle devices for inserting a delicate silicone elastomer catheter is that of shearing of the catheter by the beveled end of the needle. This danger is marked when a silicone elastomer catheter is implaced by being wholly contained within and surrounded by a full hollow needle.

With respect to devices which have utilized slotted needles for the insertion of catheters, it has in the past frequently been felt necessary to make provision for locking of the catheter assembly with respect to the slotted needle so that the catheter does not move in the slotted needle after venous puncture, since movement could result in excessive loss of blood. The utilization of the device disclosed herein obviates the need for distinct mechanisms which must be locked or unlocked, since the dispenser associated with the slotted needle in the present device automatically acts to frictionally resist such movement.

Experimental use of devices in accordance with disclosures of this application has indicated that it is possible to implant catheters up to twenty-four inches in length and perhaps more, and leave them in place for relatively long periods of time, six weeks for example. The catheter and slotted needle maintain their proper position prior to and during insertion without the necessity of additional locking and unlocking mechanisms. The forwarding mechanism in cooperation with the stiffener and elastomeric catheter gives excellent control to optimize the insertion and forwarding process. The dangers of catheter shearing or puncture and patient trauma are reduced.

The guide provided inside the dispenser permits even forwarding of the catheter and reduces the chance of binding or kinking of the catheter or stiffener. The guide cooperates with a stop on the dispenser to prevent deformation of the catheter by preventing rotation of the dispenser past the point at which the end of the catheter is adjacent the outlet on the last turn of the catheter.

The dispenser may be quickly and easily disassembled to remove the needle from the patient after catheter insertion.

The catheter insertion device disclosed herein includes a catheter dispenser which has a catheter receptacle formed by an inwardly-facing wall for receiving a catheter therewithin. The dispenser has a catheter outlet and means for rotating the circumferential wall with respect to the outlet. A needle having a pointed distal end and proximal end secured to the dispenser outlet is provided. A catheter is wound in the receptacle inside the inwardly-facing wall of the dispenser, the catheter extending through the dispenser outlet with its distal portion lying in the needle. A stiffener extends through the catheter urging the catheter against the inwardly-facing wall of the catheter dispenser. Guide means are provided in the dispenser engaging a portion of the catheter near the dispenser outlet to guide the catheter towards the outlet as the receptacle is rotated.

The catheter dispenser may include a base having a slotted catheter outlet and a second member which forms the catheter receptacle, the dispenser including means which releasably engage these first and second members in rotating relationship for movement of the catheter through the outlet.

In a preferred embodiment of the device, the dispenser has a base and receptacle which are rotatably secured by a spindle extending upwardly from the base through an aperture in the top wall of the receptacle. The spindle is split into a plurality of yieldable fingers having a circumferential detent bead to engage the receptacle. A release button rides atop the fingers, and may be depressed to urge the fingers together assisting in release of the receptacle. The utilization of such structure permits ready and smooth release of the receptacle from above the dispenser, without the necessity for manipulations under the dispenser which might cause the needle in place to be painfully raised during release.

The guide means may be a flexible elongate member extending along the walls of the receptacle between the portion of the catheter closest to the dispenser outlet and successive turns of the catheter. A shoulder stop may be provided to engage the member to positively stop rotation of the receptacle at a predetermined point in the dispensing of the last turn of the catheter.

For a more complete understanding of the present invention and for further objects and advantages thereof, reference may now be had to the following description taken in conjunction with the accompanying drawings, in which.

The catheter insertion device illustrated includes a catheter dispenser generally indicated by the reference numeral 10 secured to a slotted needle. Dispenser 10 is formed by the releasable engagement of a catheter receptacle 14 and a base 16.

Figures 6, 7, 8:
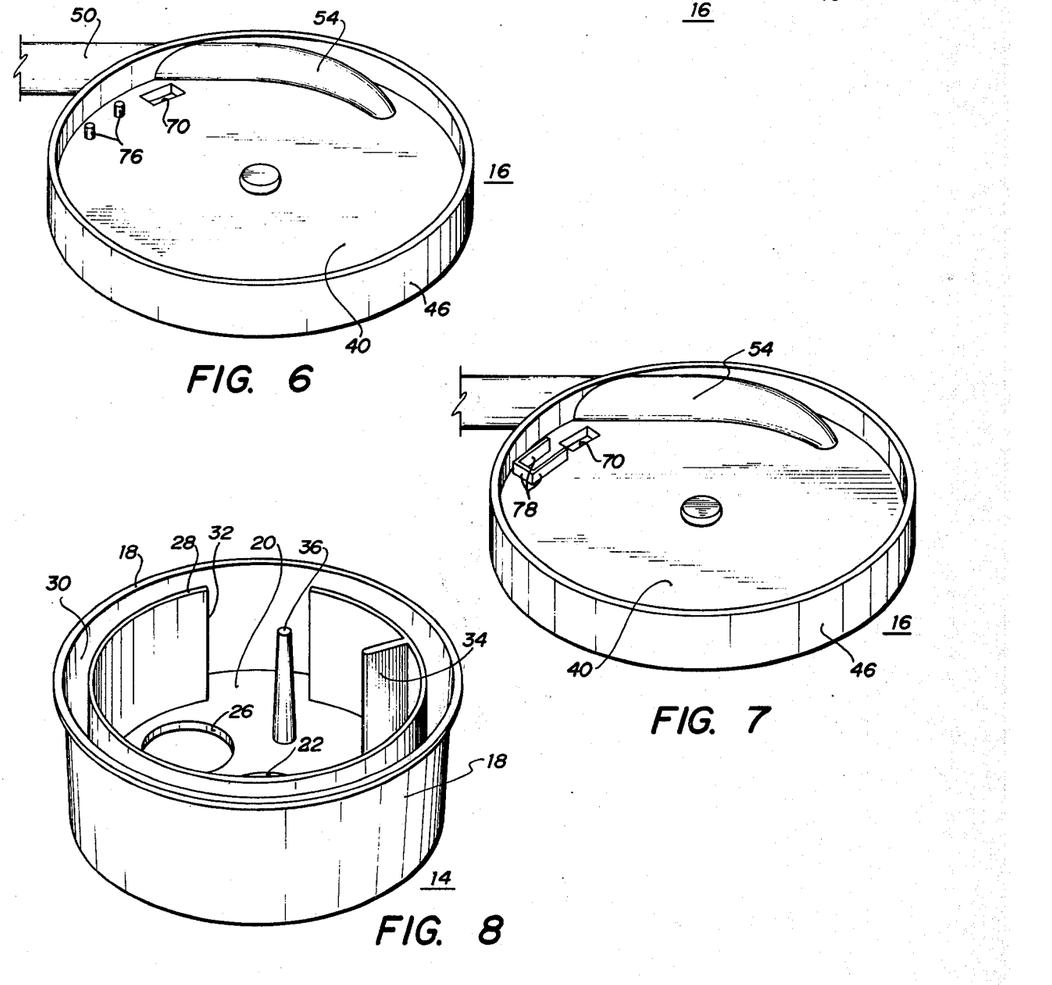
FIG. 6 is a view similar to FIG. 5, with the base member shown prior to mounting of the flexible guide thereon.
FIG. 7 is a view similar to FIG. 6, illustrating an alternate embodiment of the means for securing the guide to the base member.
FIG. 8 is a perspective view of the top member or receptacle of the device shown in FIG. 1.
Figure 9:
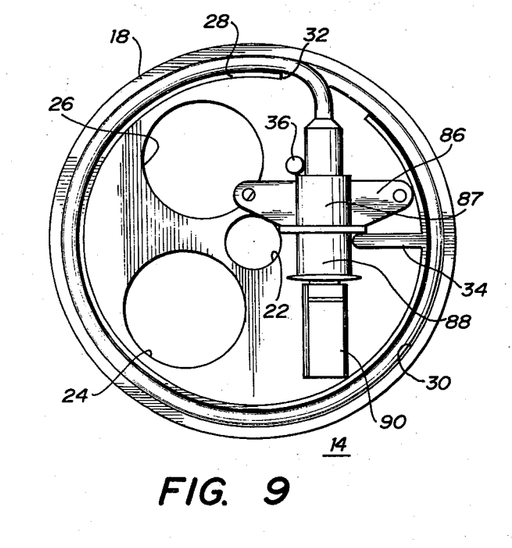
FIG. 9 is a plan view of the receptacle shown in FIG. 8.

The catheter receptacle 14, which may be fabricated as an integrally molded plastic member, comprises a cylinder defined by a circumferential outer wall 18. A flat top wall 20 extends across one end of cylindrical wall 18. A central mounting aperture 22 is formed in top wall 20. In addition, a pair of offset apertures 24 and 26 are provided in top wall 20. Receptacle 14 is provided with an inner cylindrical wall 28 extending axially from top wall 20, defining an annular space 30 between outer receptacle wall 18 and the inner wall 28. The thickness of wall 28 is increased at the top of space 30 to reduce the width of space 30 at its juncture with top wall 20. The cylinder formed by wall 28 is not complete, but is provided with a gap 32 which provides a means for passage between the central area of receptacle 14 encompassed by inner wall 28 and the annular space 30 through which a catheter may be passed. A catheter hub restraining wall 34 extends radially inwardly from inner wall 28 near the gap 32. A catheter hub restraining post 36, complementing wall 34, is spaced from wall 34 so that a catheter hub may be placed between restraining wall 34 and post 36.

At the lower end of receptacle 14, outer wall 18 is provided with an outwardly turned bearing lip or flange 38 for engagement with the base 16.

Figures 1, 2, 3, 4:
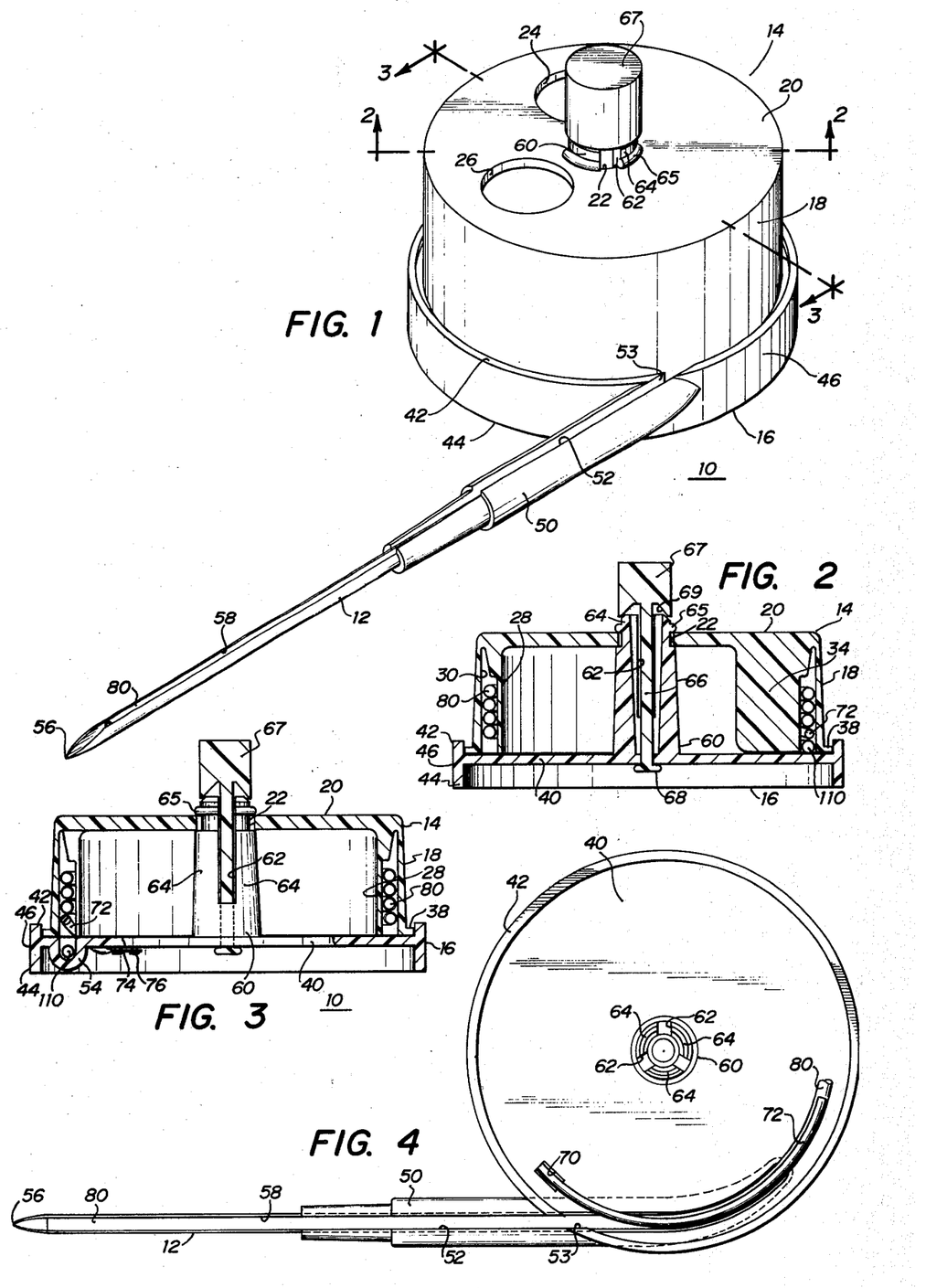
FIG. 1 is a perspective view of the catheter insertion device constructed in accordance with the present invention.
FIG. 2 is a vertical cross section taken along the line 2—2 in FIG. 1 (with the proximal portion of the catheter removed for simplicity)
FIG. 3 is a vertical cross section taken along the line 3—3 in FIG. 1 (with the proximal portion of the catheter removed for simplicity)
FIG. 4 is a top view of the base member of the device shown in FIG. 1 (with the proximal portion of the catheter and release button removed for simplicity)
Figure 5:
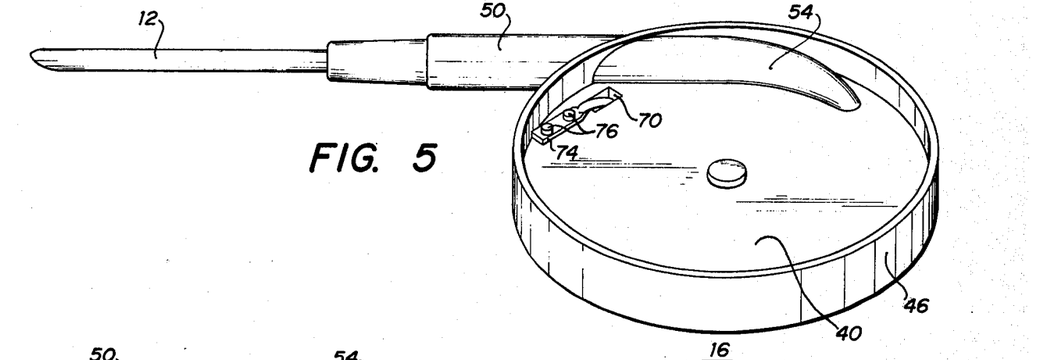
FIG. 5 is a perspective view of the bottom of the base member shown in FIG. 4.

Base 16, which may likewise be fabricated as an integrally molded plastic article, has as its major portion a flat plate 40 in the shape of a circle. Plate 40 is provided with a circumferential upper flange 42 and lower flange 44 at the intersection of a cylinder 46 with the periphery of base plate 40.

Needle hub 50 is formed integrally on the outside of cylinder 46, and is provided with a longitudinal slot 52 running the entire length of needle hub 50. Cylinder 46 has a catheter outlet slot 53 which communicates with the longitudinal slot 52 of needle hub 50. In combination, the needle hub slot 52 and outlet slot 53 provide a channel communicating from the interior of base 16 encompassed by cylinder 46 with the outer end of needle hub 50. Base plate 40 is provided with a channel or guide depression 54 formed circumferentially in its surface leading into the outlet slot 53.

Hollow slotted needle 12 is provided with a pointed distal tip 56 suitable for piercing and a longitudinal slot 58 running its entire length. Needle 12 is secured to needle hub 50 so that slot 58 is registered with the slot 52 of needle hub 50. Needle 12 may be secured to hub 50 by any convenient means, such as by molding or a tab-in-groove lock. There is thus provided a channel for moving a catheter from the interior of base 16 to the distal point 56 of needle 12, with a continuous slot providing access to that channel by the catheter outlet slot 53, needle hub slot 52 and needle slot 58.

A mounting spindle 60 is formed integrally on the central portion of base plate 40. Mounting spindle 60 extends axially upward from base plate 40 and its upper portion is trifurcated by longitudinally extending slots 62 to form three yieldable spindle fingers 64 as the upper portion of spindle 60. A detent bead 65 is formed on spindle 60 circumferentially around the fingers 64 near the top of spindle 60.

Spindle 60 cooperates with mounting aperture 22 on receptacle 18 to secure receptacle 18 to base 16 in rotating engagement. Spindle 60 extends upwardly through the aperture 22 in top wall 20 of receptacle 18 so that the detent bead 65 restrains top wall 20 and the top end 68 of spindle 60 extends above the receptacle 18. In this position, the receptacle mounting flange 38 slidingly confronts the periphery of plate 40 on base 16. So mounted, the base 16 and receptacle 18 form the dispenser 10 and the receptacle 18 may be rotated with respect to base 16.

Spindle 60 is hollow throughout its length and receives a release button shaft 66 having a release button 67 formed integrally at the top thereof. Release button 67 is secured in position over the top of fingers 64, as illustrated in FIGS. 2 and 3. A mounting stop 68 formed on the bottom of shaft 66 as it extends through base plate 40 prevents upward movement of shaft 66 within the spindle 60. Release button 67 has an inner frustoconical surface 69. On depression of button 67, the surface 69 acts to press the fingers 64 inwardly together to assist in disengaging head 65 from receptacle 18.

Base 16 is provided with a guide mounting aperture 70 through the periphery of plate 40 near the catheter outlet slot 53. Catheter guide means in the form of an elongate flexible guide rod 72 extends upwardly from plate 40 through aperture 70. Guide rod or finger 72 may be in the form of a thin solid rod formed from some relatively stiff but still yieldable and flexible material such as polyethylene or nylon. The lower end of guide 72 is flat so as to provide a convenient mounting plate 74. As illustrated in FIGS. 5 and 6, the guide 72 may be secured to base 40 on the underside of base 40 by means of pegs 76 integrally formed on the underside of base 40 adjacent the aperture 70. Corresponding holes on the mounting plate 74 of guide 72 are fitted over the mounting pegs 76 in assembly of the device, and then the pegs are subjected to melting action, as by ultrasonic means, to bond the mounting plate 74 in position on the pegs 76. Alternatively, as illustrated in FIG. 7, plastic mounting ribs 78 may be formed on the underside of plate 40 forming a raised "U" which is open in the direction of aperture 70. In this embodiment, the guide mounting base 74 may be placed against plate 40 surrounded by ribs 78, and the ribs subjected to similar melting action to bond the base 74 and thus the guide 72 into position extending through aperture 70. The end of guide rod 72 opposite the mounting base 74 is a free end 79.

No special preset curvature is formed in rod 72, so that prior to assembly in the device, it may extend linearly up and out from the aperture 70. The free end 79, when unrestrained, extends to about the height of the receptacle 14 and extends outwardly of flange 46. When loaded into the assembled dispenser, with the receptacle 18 in position on base 16, the guide 72 is restrained in a circumferential path, as shown in FIG. 4, defined by the annular space 30 in receptacle 18. If desired, the guide could be precast to conform to such circumferential path.

Figure 10:
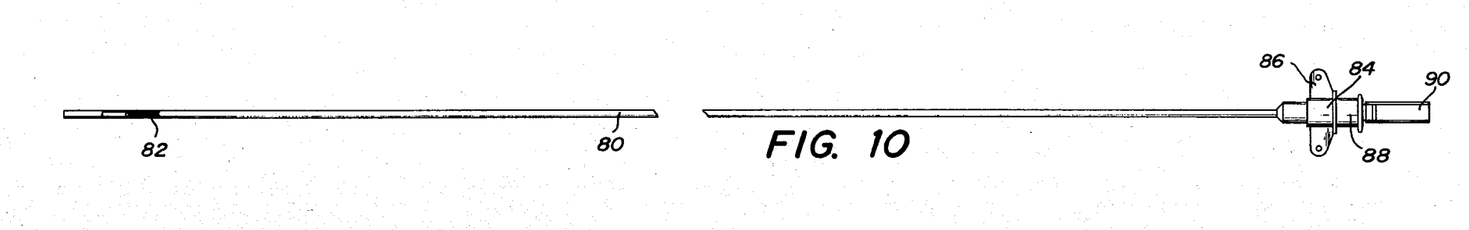
FIG. 10 is a fragmented, partially cut-away view of the catheter, stiffener and catheter hub and plug used in the device illustrated in FIG. 1, with those portions straightened out for ease of illustration.
Figure 11:
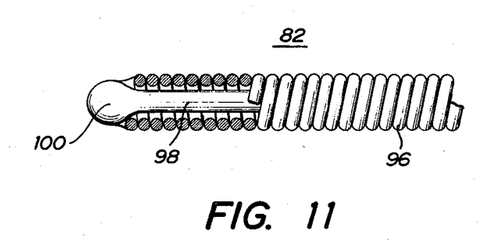
FIG. 11 is a partially cut-away plan view of the distal portion of the stiffener illustrated in FIG. 10.
Figure 12:
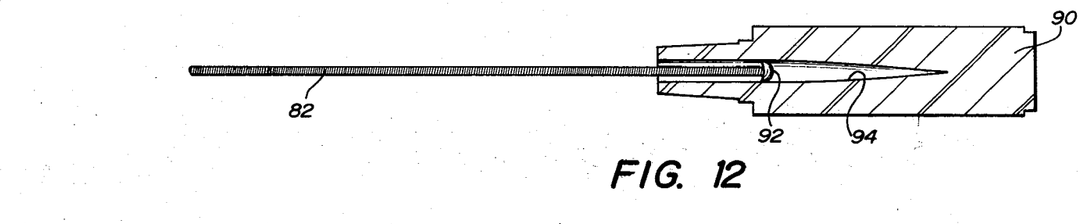
FIG. 12 is a sectional view of the proximal portion of the stiffener with catheter plug illustrated in FIG. 10.

A catheter 80 with interiorly disposed stiffener 82 is wound inside receptacle 18 and extends outwardly through outlet slot 53 so that it lies in needle 12. The structure and arrangement of the catheter 80 and stiffener 82 are illustrated in FIGS. 10—12. Catheter 80 is secured at its proximal end in a catheter hub 84 having wings 86 and providing a conventional female Luer fitting 88 for connection of a fluid source to the catheter 80 through catheter hub 84. A Luer plug 90 is secured in fitting 88 to block off the proximal end of the catheter hub 84. Catheter 80 if formed from a silicone elastomer tubing such as that marketed under the trademark "SILASTIC". The proximal end of stiffener 82 is carried by plug 90, and is secured thereto by the wedging of expanded end 92 on stiffener 82 into the central channel 94 provided in plug 90.

Stiffener 82 is comprised of a closely-wound wire helix 96 which surrounds a central strip of wire 98. The central strip 98 extends the entire length of stiffener 82. The central stiffening strip 98 and helix 96 are secured at their distal end by welding at rounded distal tip 100. In addition to strip 98, a stiffer central core wire (not shown) may be utilized to give additional stiffness, and typically would be extended from the proximal end of stiffener 82 at 92 to within about two inches of the distal tip 100. The stiffener 82 is one which has been used in the prior art as a guide in certain cardiovascular diagnostic procedures and in forwarding of subclavian silicone elastomer catheters. Its use in the environment of this invention is not believed to have been previously known.

Figure 13:
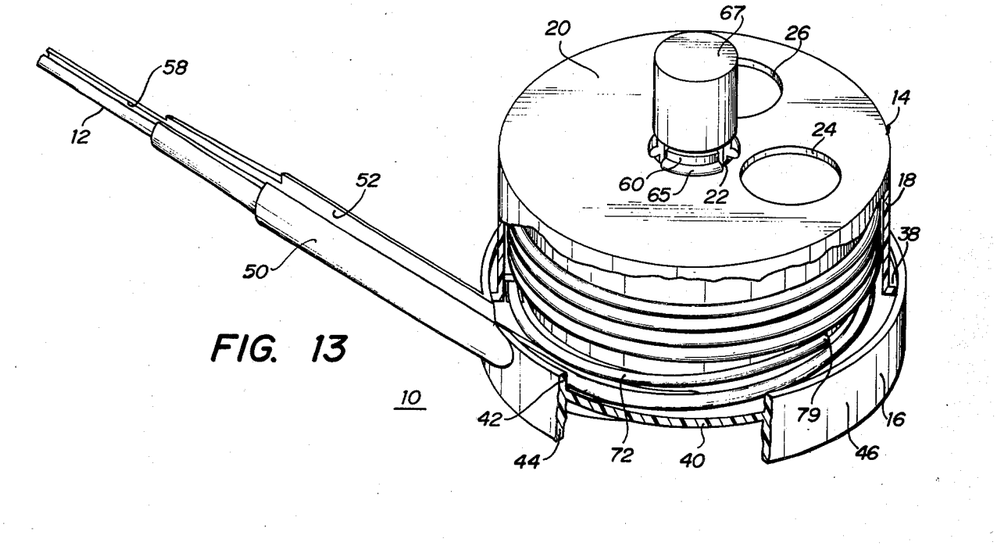
FIG. 13 is a perspective view of the device of FIG. 1 with the wall of the receptacle partially cut away, illustrating the device prior to utilization.

In the assembled device 10, the catheter 80, assembled with stiffener 82 as indicated in FIG. 10, are loaded inside the receptacle 14 of dispenser 10, with the distal end of the catheter 80 and stiffener 82 extending outwardly into needle 12. Catheter hub 84 is positioned in the portion of receptacle 18 enclosed by inner wall 28, with the hub 84 positioned between the wall 34 and post 36 as indicated in FIG. 9. Catheter 80 extends from hub 84 through the gap 32 in wall 28 into the annular space 30 between inner wall 28 and outer wall 18. The catheter 80 with its interiorly disposed stiffener 82 is wound in the annular space 30, with each successive turn coming closer to the base 16. Stiffener 82 causes the stiffened catheter to be urged outwardly against the inwardly-facing wall provided by outer cylinder 18. The distal portion of catheter 80 is threaded out through guide depression 54 and slot 53 on base 16 so that it lies in the needle hub 52 and needle 12. The distal tip of catheter 80 preferably is located just at the beveled end of needle 12, and is maintained in that position by the frictional engagement of receptacle wall 18 with the catheter 80. The free end 79 of guide 72 is disposed in the annular space 30 so that it separates the lowermost turn 110 of catheter 80 from the other turns of catheter 80 located above it in receptacle 18. In the ready-for-use condition illustrated in FIG. 13, the turns of the catheter 80 located above guide 72 in the annular space 30 act upon guide 72 to press it downwardly toward base 16. With the catheter and guide so loaded, the dispenser 10 is assembled and ready for utilization.

In use, the dispenser 10 is held so that the receptacle 14 and needle slot 58 are oriented away from the skin of the patient at the injection site. The needle 12 is inserted through the skin into a vein at the desired point of entry, as indicated by the orientation of the dispenser 10 in FIG. 15. With the needle 12 in position in the vein, the catheter 80 and stiffener 82 are forwarded into the vein together by rotation of the receptacle 14 in the clockwise direction, indicated by the arrow shown on receptacle 14 in FIG. 13. The forwarding action is best appreciated by reference to FIGS. 13 and 14, by which it will be seen that the action of guide 72 serves to continually guide the portion of the catheter 80 coming towards outlet 53 downwardly so that it lines up with such outlet. As the forwarding operation proceeds by continuing rotation of receptacle 18, progressively less of the catheter 80 remains above the guide 72. When only one turn of catheter 80 remains in receptacle 14, no portion of catheter 80 remains above the guide 72 to restrain the free end 79 of the guide 72 from its natural bias upwards. Since the guide 72 extends upward from base 16 at an angle which would cause the free end 79 when unrestrained to stand as high as the receptacle, free end 79 rides directly to the top of annular space 30 adjacent top wall 20. In such posititon, an automatic stop 112 is provided by the wall 28 at its edge forming the gap 32. Stop 112 is provided at that edge by the thickened portion at the top of wall 28. Once only the last turn of the catheter remains on the receptacle 14, and the receptacle 14 is rotated to the position illustrated in FIG. 14, stop 112 engages guide 72 to positively stop rotation of the receptacle 14 with respect to base 16. This prevents over-running of the end of catheter 80 past outlet 50, which could deform the catheter 80 and stiffener 82 by kinking them at the outlet 50.

During the forwarding operation, combination of the helical stiffener and silicone elastomer catheter together with the rotating dispenser forwarding mechanism and slotted needle cooperates to maximize the opportunity for successful catheter placement. The guide assists in the smooth control of the catheter.

The rotating dispenser enables the user to exercise careful control over the forwarding process. The use of the helical stiffener and elastomeric tubing with such well-controlled forwarding improves the negotiation of long and sometimes tortuous vessels with the delicate catheter while reducing the risk of trauma. It appears that the helical stiffener leads the silicone elastomer catheter through the vein as the dispenser is reeled forward.

While reversal of the dispenser rotation might otherwise risk grave danger of catheter shearing, the use of the slotted needle in the combination reduces the risk from the level which it otherwise might reach with the use of a delicate silicone elastomer catheter.

Figures 14, 15, 16:
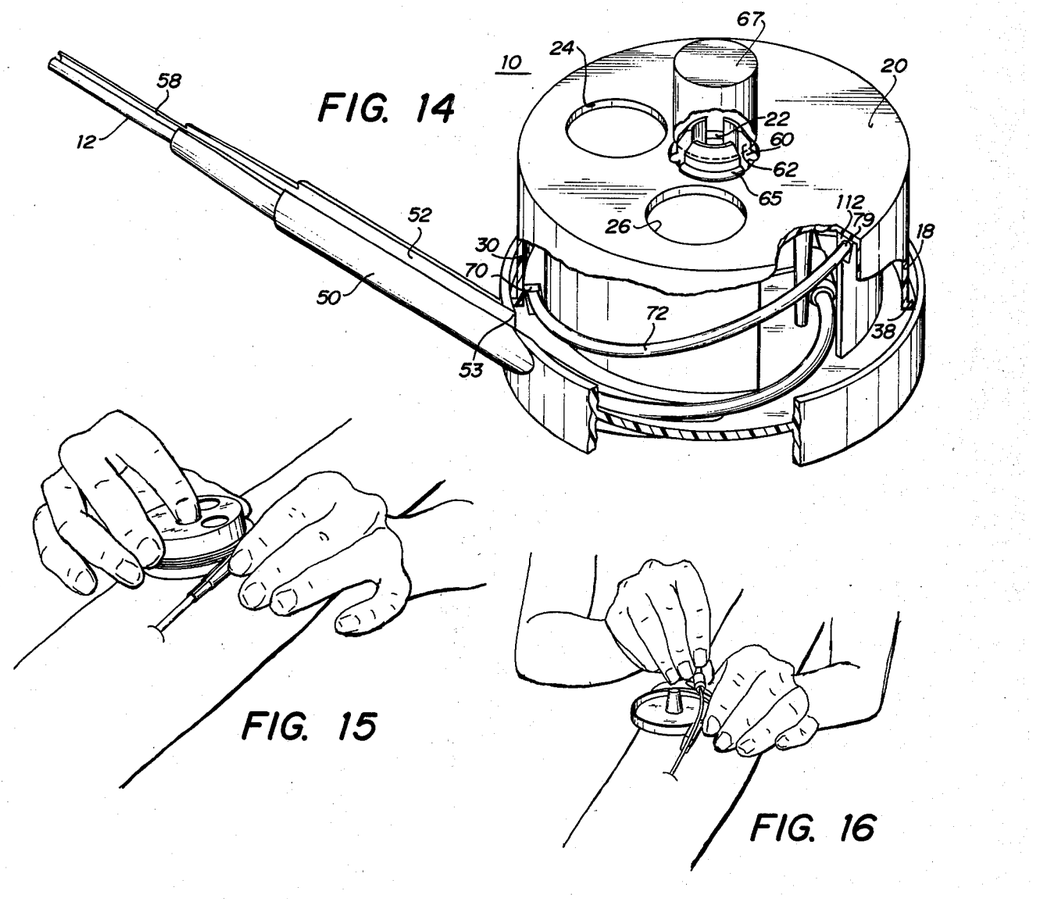
FIG. 14 is a perspective view similar to that of FIG. 13, illustrating the device after the receptacle has been rotated to insert the catheter into the body of a patient.
FIG. 15 is a perspective view illustrating the step of removing the catheter receptacle after insertion has reached the stage illustrated in FIG. 14.
FIG. 16 is a view showing the step of completing the catheter insertion prior to removal of the needle.

Once the receptacle has been rotated to the position illustrated in FIG. 14, receptacle 14 may be snapped off base 16 as illustrated in FIG. 15. The arrangement of the spindle 60 which holds dispenser 10 together permits this removal operation by engagement of the side walls 18 of receptacle 14 with the thumb and middle finger to pull upward on receptacle 14 while the forefinger presses down on the button 67 to assist release of the receptacle 18 from the detent bead 65. This separation operation is thus performed without need to reach a hand or any part thereof underneath base 16, a movement which could cause the base to the tipped up from the skin of the patient possibly causing additional trauma and bleeding. The receptacle 14 may thereafter be discarded.

If desired, the additional length of catheter remaining outside the body may be forwarded into the body in the manner illustrated in FIG. 16, by gripping the catheter hub 84 and forwarding the catheter guided by needle 12. Needle 12 can thereafter be removed and the needle 12 with attached base 16 discarded, leaving the catheter in position with the hub ready to be taped or sutured down to the skin of the patient in the conventional manner.

The dispenser 10 disclosed in this application may also be used without attachment of needle 12. In such form, the hub 50 can be mated with any suitable fitting to forward a catheter 80 from the dispenser 10 through such fitting. For example, such use could be made of dispenser 10 with needle 12 omitted in a catheter-through-catheter (CTC) insertion. In such a procedure, an initial insertion using conventional techniques is made to introduce a guide catheter. The proximal end of the guide catheter may be provided with a suitable Luer fitting to receive hub 50 of dispenser 10, whereupon a smaller principal catheter 80 may be introduced from dispenser 10 through the guide catheter.

Having described the invention in connection with certain specific embodiments thereof, it is to be understood that further modifications may now suggest themselves to those skilled in the art and it is intended to cover such modifications as fall within the scope of the appended claims.

What is claimed is:

1. A catheter insertion device comprising:
   a catheter dispenser comprised of a base having a catheter outlet and a catheter receptacle including an inwardly-facing wall for receiving a catheter therewithin, the dispenser including means engaging the base and receptacle in rotating relation;
   a needle having a pointed distal end and a proximal end secured to the dispenser outlet;
   a catheter wound inside the inwardly-facing wall of the receptacle, the catheter extending through the dispenser outlet with its distal portion lying in the needle; and
   guide means inside the dispenser engaging a portion of the catheter near the dispenser outlet to guide the catheter downwardly towards the outlet as the receptacle is rotated with respect to the base.

2. The device of claim 1, wherein said needle is a slotted needle.

3. The device of claim 1, wherein the catheter is formed from a silicone elastomer.

4. The device of claim 3, further comprising a stiffener disposed in the catheter comprising a closely wound wire helix.

5. The device of claim 1, further comprising a stop shoulder secured to the receptacle to engage said guide means at a predetermined point in the dispensing of the catheter to positively stop rotation of the receptacle.

6. The device of claim 1, further comprising a top wall on the receptacle having a central aperture, and a spindle integrally formed on the base and extending upwardly from the base and through the receptacle top wall aperture to releasably engage the receptacle and base in rotating relation.

7. The device of claim 6, wherein the upper end of the spindle is split into a plurality of yielding fingers, and further comprising a release button mounted atop the fingers so that the button may be depressed to urge the fingers together.

8. A catheter insertion device comprising:
   a catheter dispenser comprised of a base having a catheter outlet and a catheter receptacle including an inwardly-facing wall for receiving a catheter therewithin, the dispenser including means engaging the base and receptacle in rotating relation;
   a catheter wound inside the inwardly-facing wall of the receptacle, the catheter extending through the dispenser outlet; and
   guide means inside the dispenser engaging a portion of the catheter near the dispenser outlet to guide the catheter downwardly towards the outlet as the receptacle is rotated with respect to the base.

9. A catheter insertion device comprising:
   a base having a catheter outlet slot at its periphery;

a generally cylindrical catheter receptacle rotatably engaging the base to form a catheter dispenser;

a catheter wound in a plurality of turns against the cylindrical wall of the receptacle and extending through the outlet; and an elongate flexible guide secured to the base and extending along a path inside the circumferential wall of the receptacle away from a point adjacent the catheter outlet, such path lying between the turn of the catheter in the receptacle closest to the catheter outlet and the other turns of the catheter in the receptacle.

10. A catheter insertion device comprising:

a base having a catheter outlet slot at its periphery;

a generally cylindrical catheter receptacle rotatably engaging the base to form a catheter dispenser;

a catheter wound in a plurality of turns against the cylindrical wall of the receptacle and exteending through the outlet;

an elongate flexible guide secured to the base and extending along a path inside the circumferential wall of the receptacle away from a point adjacent the catheter outlet, such path lying between the turn of the catheter on the receptacle closest to the catheter outlet and the other turns of the catheter in the receptacle; and a stop shoulder fixed to the receptacle to engage the end of the guide at a predetermined point in the dispensing of the last turn of the catheter to positively stop rotation of the receptacle.

11. A catheter insertion device comprising:

a catheter dispenser having a catheter receptacle formed by an inwardly-facing circumferential wall for receiving a catheter therewithin and having an apertured top wall, a base having a catheter outlet, and means allowing rotation of said receptacle wall with respect to the outlet;

a slotted needle having a pointed distal end and a proximal end secured to the dispenser outlet;

a silicone elastomer catheter in the receptacle wound inside the inwardly-facing wall of the catheter dispenser, the catheter extending through the dispenser outlet with its distal portion lying in the needle;

a stiffener extending through the catheter including a closely-wound wire helix, urging the catheter against the inwardly-facing wall of the catheter dispenser;

a flexible guide member inside the dispenser engaging a portion of the catheter adjacent the catheter outlet to guide the catheter to the outlet as the dispenser wall is rotated;

a stop shoulder positioned in fixed relationship to the circumferential dispenser wall for engaging the guide member to positively stop rotation of the wall at a predetermined point prior to dispensing all of the catheter from the dispenser; and a spindle secured to the base and extending upwardly from the base through the aperture in the top wall of the receptacle to secure the receptacle and base in rotating relation.

12. The device of claim 11, wherein the guide member is an elongate flexible finger secured at one end to the base near the outlet and having its opposite end unattached to the dispenser and loaded between two adjacent turns of the catheter in the receptacle.

13. A catheter insertion device comprising:

a base having a catheter outlet slot at its periphery;

a generally cylindrical catheter receptacle rotatably engaging the base to form a catheter dispenser;

a needle secured to the catheter outlet; and a catheter wound in a plurality of turns against the cylindrical wall of the receptacle and extending through the outlet so that its distal end lies in the needle; and an elongate flexible guide secured to the base and extending along a path inside the circumferential wall of the receptacle away from a point adjacent the catheter outlet, such path lying between the turn of the catheter in the receptacle closest to the catheter outlet and the other turns of the catheter in the receptacle.

14. A catheter insertion device comprising:

a base having a catheter outlet slot at its periphery;

a generally cylindrical catheter receptacle rotatably engaging the base to form a catheter dispenser;

a needle secured to the catheter outlet; and a catheter wound in a plurality of turns against the cylindrical wall of the receptacle and extending through the outlet so that its distal end lies in the needle;

an elongate flexible guide secured to the base and extending along a path inside the circumferential wall of the receptacle away from a point adjacent the catheter outlet, such path lying between the turn of the catheter on the receptacle closest to the catheter outlet and the other turns of the catheter in the receptacle; and a stop shoulder fixed to the receptacle to engage the guide at a predetermined point in the dispensing of the last turn of the catheter to positively stop rotation of the receptacle.

15. A catheter insertion device comprising:

a catheter dispenser comprised of at least two separable members including a first member having a slotted catheter outlet and a second member having a catheter receptacle formed by an inwardly-facing wall thereon for receiving a catheter therewithin, the dispenser including means releasably engaging the first and second members in rotating relation;

a slotted needle having a pointed distal end and a proximal end secured to the slotted dispenser outlet with its slot in register with the slot of the dispenser outlet;

a silicone elastomer catheter in the receptacle wound against the inwardly-facing wall of the second dispenser member, the catheter extending through the dispenser outlet with its distal portion lying in the needle;

a stiffener extending through the catheter, urging the catheter against the inwardly-facing wall of the second dispenser member; and guide means inside the dispenser engaging a portion of the catheter near the outlet to guide the catheter towards the outlet upon relative rotation of the first and second members of the dispenser.

16. The device of claim 15, further comprising a spindle secured integrally to the first member of the dispenser and extending normally thereto, a top wall on the catheter receptacle having an aperture therethrough, said spindle extending through and engaging said aperture to form the means engaging the first and second dispenser members releasably in rotating relation.

17. A catheter insertion device comprising:

a base having a catheter outlet slot at its periphery;

a spindle integral with the base extending from a central portion of the base along an axis perpendicular to the major portion of the base;

a generally cylindrical catheter receptacle having a top wall with a central aperture rotatably engaging the spindle so that the end of the receptacle opposite such top wall rotatably confronts the base and the spindle extends through the top wall; and a catheter wound inside the cylindrical wall of the receptacle and extending through the outlet so that its distal end lies in the needle, whereby the catheter may be forwarded into the body of a patient by rotation of the receptacle and the receptacle may be subsequently removed from the base with one hand from above the base by digital pressure on the end of the spindle accompanied by an upward pulling force on the cylindrical wall of the receptacle in the direction away from the base.

18. A catheter insertion device comprising:

a base having a catheter outlet slot at its periphery;

a spindle integral with the base extending from a central portion of the base along an axis perpendicular to the major portion of the base;

a generally cylindrical catheter receptacle having a top wall with a central aperture rotatably engaging the spindle so that the end of the receptacle opposite such top wall rotatably confronts the base and the spindle extends through the top wall;

a needle secured to the catheter outlet; and a catheter wound inside the cylindrical wall of the receptacle and extending through the outlet so that its distal end lies in the needle, whereby the catheter may be forwarded into the body of a patient by rotation of the receptacle and the receptacle may be subsequently removed from the base with one hand from above the base by digital pressure on the end of the spindle accompanied by an upward pulling force on the cylindrical wall of the receptacle in the direction away from the base.

19. A catheter insertion device comprising:

a base having a catheter outlet slot at its periphery;

a spindle integral with the base extending from a central portion of the base along an axis perpendicular to the major portion of the base, and being split at its upper end into a plurality of yieldable fingers having a circumferential detent;

a generally cylindrical catheter receptacle having a top wall with a central aperture rotatably engaging the detent of the spindle so that the end of the receptacle opposite such top wall rotatably confronts the base and the spindle extends through the top wall;

a downwardly movable release button mounted atop the spindle having a canted inner surface for engaging the yieldable fingers; and a catheter wound inside the cylindrical wall of the receptacle and extending through the outlet, whereby the catheter may be forwarded into the body of a patient by rotation of the receptacle and the receptacle may be subsequently removed from the base with one hand from above the bass by digital pressure on the release button accompanied by an upward pulling force on the cylindrical wall of the receptacle in the direction away from the base.

20. A catheter insertion device comprising:

a base having a catheter outlet slot at its periphery;

a spindle integral with the base extending from a central portion of the base along an axis perpendicular to the major portion of the base, and being split at its upper end into a plurality of yieldable fingers having a circumferential detent;

a generally cylindrical catheter receptacle having a top wall with a central aperture rotatably engaging the detent of the spindle so that the end of the receptacle opposite such top wall rotatably confronts the base and the spindle extends through the top wall;

a downwardly movable release button mounted atop the spindle having a canted inner surface for engaging the yieldable fingers;

a needle secured to the catheter outlet; and a catheter wound inside the cylindrical wall of the receptacle and extending through the outlet, so that its distal end lies in the needle, whereby the catheter may be forwarded into the body of a patient by rotation of the receptacle and the receptacle may be subsequently removed from the base with one hand from above the base by digital pressure on the release button accompanied by an upward pulling force on the cylindrical wall of the receptacle in the direction away from the base.

* * * * *